United States Patent [19]

Oka et al.

[11] Patent Number: 4,597,848
[45] Date of Patent: Jul. 1, 1986

[54] ELECTRODE FOR MEASUREMENT OF ION ACTIVITY

[75] Inventors: Syotaro Oka, Muko; Shu Tahara, Nagaokakyo; Yaichiro Shibazaki, Hino, all of Japan

[73] Assignee: Shimadzu Corporation, Kyoto, Japan

[21] Appl. No.: 675,517

[22] Filed: Nov. 28, 1984

Related U.S. Application Data

[63] Continuation of Ser. No. 272,210, Jun. 10, 1981, abandoned.

[30] Foreign Application Priority Data

Jun. 16, 1980 [JP] Japan .................. 55-81844
Jun. 16, 1980 [JP] Japan .................. 55-81845
Aug. 26, 1980 [JP] Japan .................. 55-117990

[51] Int. Cl.$^4$ ............................ G01N 27/46
[52] U.S. Cl. .................... 204/418; 204/296
[58] Field of Search .............. 204/416-420, 204/296

[56] References Cited

U.S. PATENT DOCUMENTS

| | | | |
|---|---|---|---|
| Re. 24,222 | 9/1956 | Patnode et al. | 204/418 |
| 3,398,079 | 8/1968 | Arthur et al. | 204/420 |
| 3,556,950 | 1/1971 | Dahms | 204/419 |
| 3,562,139 | 2/1971 | Leitz | 204/296 |
| 3,864,233 | 2/1975 | Dietrich et al. | 204/419 |
| 3,964,988 | 6/1976 | Riseman et al. | 204/419 |
| 4,115,209 | 9/1978 | Freiser et al. | 204/418 |
| 4,135,999 | 1/1979 | Schindler et al. | 204/418 |

FOREIGN PATENT DOCUMENTS 33-8515  9/1958  Japan .

OTHER PUBLICATIONS

"Anal. Chem.", vol. 53, No. 4, (1982), pp. 588-593.
Imato et al., "Anal. Chem.", vol. 52, (1980), pp. 1893-1896.
Martin et al., "Anal. Chem.", vol. 52, (1980), pp. 562-565.
Carson et al., "Anal. Chem.", vol. 27, No. 3, (1955), pp. 472-473.
"Anal. Chem.", vol. 53, May, 1981, pp. 902-904.
Eguchi et al., "Membrane", 3(4), pp. 289-294 (1978) Permselectivities of Amphoteric Ion-Exchange Composite Membrane I.
Eguchi et al., "Membrane", 3(5), pp. 367-373 (1978) Permselectivities of Amphoteric Ion-Exchange . . . II.

Primary Examiner—T. Tung
Attorney, Agent, or Firm—Stiefel, Gross, Kurland & Pavane

[57] ABSTRACT

There are disclosed an ion selective electrode which adopted a solid polymer membrane with specific ion exchangers, and an apparatus and measuring method with the above-mentioned electrode. The electrode is suitable for the quantitative chemical analysis of a specific ion activity in electrolytic solutions with various foreign ions, for example an activity of chloride ion in blood, urine or any other biological solutions.

15 Claims, 6 Drawing Figures

ELECTRODE FOR MEASUREMENT OF ION ACTIVITY

This is a continuation, of application Ser. No. 272,210, filed June 10, 1981, now abandoned.

BACKGROUND OF THE INVENTION

1. Field of the Invention

This invention relates to an electrode for measuring an ion activity (concentration x activity coefficient) in a solution. More particularly, this invention relates to an electrode which uses a solid polymer membrane of an ion exchanger as an ion selective substance and is useful for the quantitative analysis of a specific anion or cation in the presence of various foreign anions or cations, and to an apparatus utilizing said electrode.

2. Description of the Prior Art

Currently available methods for the measurement of the activity of chloride ion in the blood through analysis for electrolytic content include the coulometric method, the ion electrode method and so forth. The coulometric method, when applied to a sample requires that one first remove corpuscular components from the whole blood and isolate the plasma and serum, dilute the isolated plasma and serum with a suitable diluent and subject the resultant dilution product to coulometric analysis. The ion electrode method involves inserting an ion electrode incorporating an ion sensitive substance into a given sample and measuring the electric potential which is generated between the ion sensitive substance and the sample. Various ion electrodes have been developed. These are typified by a glass electrode intended for the measurement of hydrogen ions (pH). If there were developed an ion selective electrode capable of directly measuring the concentration of chloride ion in the blood, the aforementioned procedures such as the centrifugation and dilution of the blood cells could be eliminated while still being able to determine the true concentration of chloride ion in the blood to be determined. A solid membrane electrode formed by using AgCl as its principal component is typical of ion electrodes sensitive to chloride ion. While this electrode has an advantage that it offers low electric resistance and permits easy measurement of electrode potential difference, it nevertheless has a disadvantage that, when used on a vital sample, it is possibly smeared with various components other than the objective ions such as, for example, proteins to a point where it exhibits degraded sensitivity and retarded response and loses in reproducibility of measurement and selectivity for chloride ion. A liquid membrane electrode has already been developed as an electrode sensitive to various anions. It is preprared by having an ion sensitive substance passed into and deposited fast in a porous carrier. Because of this particular construction, it is difficult to clean and suffers from a short service life. When this liquid membrane electrode is applied to a vital sample, it is smeared with the coexistent substances (such as, for example, proteins and blood cells) of the sample similarly to the solid membrane electrode of AgCl and, consequently, is degraded in sensitivity and response speed. (Refer to U.S. Pat. No. 3,429,785.) One version of the liquid membrane electrode has made use of an ion exchanger (Coetzee, C. J. & Freiser, H.: Anal. Chem. 1968, 40, 2071 & 1969, 41, 1128–1130). This version has not been immune from the problems common to all the liquid membrane electrodes. An electrode using a so-called "heterogeneous membrane", which has an ion carrier such as Valimomycin incorparated in a polymeric material, has been introduced (U.S. Pat. No. 3,753,887). In terms of performance, however, this electrode has never proved to excel the liquid membrane electrode mentioned above.

SUMMARY OF THE INVENTION

An object of this invention is to provide an ion selective electrode for measuring an ion activity, which uses as an ion sensitive substance thereof a solid membrane of an anion-exchanger or cation-exchanger.

A further object of this invention is to provide an ion selective electrode for the measurement of an ion activity, which uses as an ion sensitive substance thereof a solid membrane of an anion-exchanger or cation-exchanger and further incoporates, in part, an ion-exchange group of opposite polarity, i.e. a cation-exchange or anion-exchange group.

Another object of this invention is to provide an apparatus for the measurement of a specific ion activity by use of the electrode mentioned above.

DETAILED DESCRIPTION OF THE INVENTION

This invention has been perfected on the basis of a new knowledge that, as an ion sensitive substance for the ion selective electrode, a solid membrane made of an anion-exchange or cation exchange synthetic resin is effective in the measurement of the potential difference of ion activity.

This invention has also been accomplished on the basis of another new knowledge that use of a so-called amphoteric ion-exchange membrane (use of an ion-exchange resin which, unlike the amphoteric ion-exchange resin as conceived from the conventional generally accepted definition, uses an ion-exchange group of one polarity as a principal component and additionally incorporates an ion-exchange group of the opposite polarity) is effective in the measurement of the potential difference of ion activity.

It is still another object of this invention to provide an apparatus which installs therein the electrode using such a specific solid membrane for the measurement of an ion activity and which enables an ion activity in a varying sample, particularly a vital sample, to be measured without requiring the sample to be pretreated.

In the ion selective electrode of the present invention for the measurement of an ion activity, the ion selective substance is used in the form of a solid membrane. The term "solid membrane" as used in this invention has the same meaning as generally accepted in the technical field to which this invention pertains. For use in this invention, this solid membrane is desired to have a homogeneous texture.

The anion-exchange or cation-exchange membrane for use in this invention may be selected from those known in the art.

Cross-linked polymers of the class generally adopted for the preparation of well-known ion-exchange resins can be cited as synthetic resins which are usable for forming the backbone of the ion-exchanger contemplated for the production of the solid membrane mentioned above. Specific examples are polystyrene, styrene-divinyl benzene copolymer, styrene-butadiene copolymer, phenol resins, polyacrylonitrile, polymethacrylic acid, polyvinyl pyridine, polyvinyl alcohol, glycidyl methacrylate and dimethylaminoethyl methacrylate. Among these polymers, styrene-divinyl benzene copolymer, styrene-butadiene copolymer and phenol resins are desirable choices. Styrene-divinyl benzene copolymer and styrene-butadiene copolymer are better choices. And, styrene-divinyl benzene is the best choice.

Examples of the cation-exchange group desirably contained in the synthetic resin include sulfonic acid group, phosphonic acid group, arsonic acid group, carboxylic acid group and selenonic acid group. Examples of the anion-exchange group desirable are quaternary ammonium group, quaternary phosphonium group and tertiary sulphonium group. Typical examples of quaternary ammonium group include $-N^+H_3$ and $-N^+(R)_3$ wherein R is a lower alkyl group (e.g., methyl or ethyl) or benzyl group.

Examples of cation-exchange and anion-exchange solid membranes are membranes having the properties of those marketed under trademark designations of Dowex 50WX, MSC-1, CCR-2 and A-1 (cation-exchange) and Dowex IX,2X, II, 21K, WGR, MSA-1 and MWA-1 (anion-exchange), which are invariably the products of The Dow Chemical Company.

The solid membrane for use in this invention may be in a modified form which is obtained by incorporating as part of the cation-exchange group-containing membrane or anion-exchange group-containing membrane an ion-exchange group of opposite polarity.

In this case, either commercial products satisfying the requirement of the invention or those prepared by having cation-exchange or anion-exchange membranes reacted upon by compounds possessing a desired anion-exchange group or cation-exchange group may be used.

For example, incorporation of a sulfonic acid type cation-exchange group in a desired proportion into a quaternary ammonium salt type anion-exchange resin can be accomplished by soaking the anion-exchange membrane in an alkyl-benzene sulfonic acid solution, then elevating the temperature of the membrane and the solution and allowing the membrane to undergo reaction in the solution for a stated period.

Conversely, incorporation of a quaternary ammonium salt type anion-exchange group into a sulfonic acid type cation-exchange membrane, for example, can be effected by chlormethylating the cation-exchange membrane and subsequently treating the chloromethylated membrane with an amine.

Otherwise, a copolymer satisfying the requirement of this invention may be obtained by mixing a monomer(or a low-molecular polymer) possessing an anion-exchange group with a monomer (or a low-molecular polymer) possessing a cation-exchange group in a proper ratio and subjecting the resultant mixture to a cross-linking treatment under copolymerization conditions.

The term "incorporation" used in this specification is applicable also to cases wherein anionic or cationic groups have been substituted with ionic groups of opposite polarity or such ionic groups of opposite polarity have been added to anionic or cationic groups.

The content in a given ion-exchanger of an ionic group of opposite polarity can be determined, for example, by measuring the surface concentration of the specific ionic group in the resin by means of an electron microprobe X-ray analyzer. The exact content of the specific group in the resin would be difficult to determine. The content in a quaternary ammonium type exchanger of a sulfonic acid group (reverse cationic group), for example, may be expressed in terms of the 100 arbitrary units of the saturated concentration of the sulfonic acid group in the ion-exchanger. The results of the test conducted by the inventors have shown that incorporation of the reverse ion-exchange group within the range of from 40 to 10 arbitrary units, particularly from 30 to 20 arbitrary units, is desirable for the purpose of this invention.

In other words, the ratio of the exchange capacities of the two reverse ionic groups contained in the amphoteric ion-exchange membrane is desired to fall within the range of from 40:60 to 0.5:95.5, preferably from 10:90 to 30:70. This is equivalent to a statement that the amphoteric ion-exchange membrane is desired to contain either of the two ion-exchange groups in a significantly larger amount than the other.

As an ion sensitive substance, the ion-exchange membrane as described above is put to use as suitably mounted on a varying type of electrode. An electrode of the inner-electrode type, for example, may be desirably obtained by molding the resin in the shape of a film membrane, cutting the membrane to a desired size, setting the resultant membrane in position within a cylinder produced in advance as the support for the electrode and stretching the membrane taut with the aid of an O-ring, for example. An electrode of the wire type may be advantageously obtained by immersing a wire (0.05 to 1.0 mm in diameter, for example) in a solution containing the resin and causing the wire to be coated with the resin. The thickness of the membrane is preferred to be in the range of from 10 to 1000 $\mu$m.

The aforementioned anion-exchange or cation-exchange membrane, the amphoteric ion-exchange or cation-exchange membrane, the electrode incorporating such membrane, the material, treatment and procedure to be adopted for the preparation of such synthetic resins can be suitably selected in accordance with the kinds and conditions for the sample and the objective ion.

Now, to facilitate the comprehension of this invention, the operation and function of the electrode of this invention for the measurement of an ion activity will be described based on the principle of the ion electrode method.

In the first place, the present invention uses a specific ion-exchange membrane as an ion sensitive substance for the ion selective electrode. Generally, ion-exchange membranes are utilized as diaphragms in electrolytic cells for the purpose of preventing electrolyzates from mingling with electrolyte solutions and consequently impairing efficiencies of electrolysis or as ion filters for the concentration or deionization of seawater. In such applications, the electric current passed to the membranes serves to drive ions and accelerate screening of ions. So far, the studies on the ion-exchange membranes have been limited to applications wherein the flow of electric current is utilized for causing migration or passage of specific ions. It has now been found that when the ion-exchange membrane is placed between two solutions containing an ion exhibiting specificity to the membrane in different concentrations and the electric potential is measured in the boundaries between the two solutions and the membrane instead of causing any flow of electric current, the potentials found in the boundaries have some bearing upon the activity or concentration of the specific ion present in the solutions.

By the inventors, it has been ascertained that the electric potentials in the boundaries formed between the solid membrane of the anion-exchanger or cation-exchanger of the present invention and the two solutions are satisfactorily in agreement with those found by the formula of Nernst and that the velocity of the generation of such potentials corresponds instantaneously to the change in the ion concentration in the solutions. (A further detail will be given afterward.)

Now, let $e_1$ and $e_2$ stand for the electric potentials on the boundaries and $a_i$ for the ratio of the activities of the ion in the two solutions bordering on the two surfaces of the membrane, the following equation is satisfied:

$$E = e_1 + e_2 = E^0 + 2.303 \frac{RT}{nF} \cdot \log a_i \text{ (volts)}$$

wherein, R denotes a gas constant, F a Faraday constant, T an absolute temperature, n the valency of the ion participating in the reaction and $E^0$ the standard potential. Where the ion is monovalent and the temperature is 25° C., the foregoing equation is expressed as follows.

$$E = E^0 + 0.0591 \log a_i$$

This means that E is varied by about 59 mV where the activity of the ion in the solution on one side of the membrane varies by 10 times.

Now, the invention will be described specifically below with reference to a working example.

Figure 1:
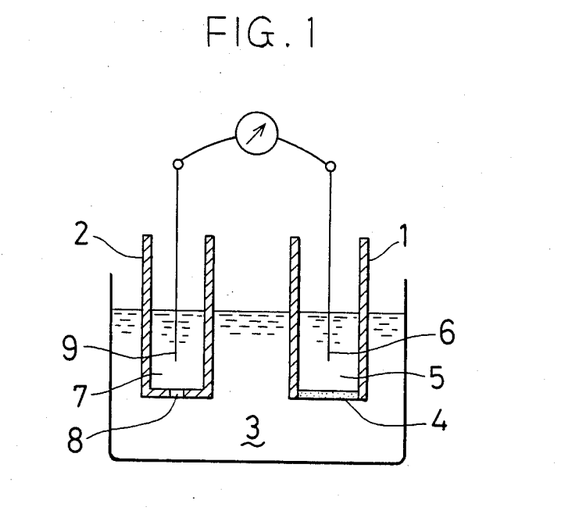
FIG. 1 is a schematic diagram showing in side elevation a basic apparatus using the electrode of the present invention for the measurement of an ion activity.

FIG. 1 represents a basic apparatus using the electrode of this invention for the measurement of an ion activity. In the diagram, 1 denotes an indicating electrode (ion selective electrode) body, 2 a reference electrode body and 3 a sample solution to be measured for ion activity. The indicating electrode body 1 has an open bottom, which is closed with an ion-exchange membrane 4.

The indicating electrode body 1 is filled with an inner solution 5 for the electrode. Thus, the ion-exchange membrane 4 partitions the sample solution 3 and the inner solution 5 for the electrode. The inner solution 5 for the electrode contains, in a known concentration (or known activity), an ion of the type for which the ion-exchange membrane 4 exhibits selectivity. Where a monovalent ion is subjected to measurement, the ion-exchange membrane 4 is in the form of a monovalent anion-exchange membrane and the inner solution 5 for the electrode is a solution of a monovalent anion such as Cl ion, i.e. the solution of KCl, for example. The electrode 6 is inserted into the inner solution 5 for the electrode. As the inner electrode 6, a stable electrode of the monopolar potential type such as, for example, a Calomel electrode or silver chloride electrode is used. The reference electrode body 2 is filed with an inner solution 7 for the electrode which is the same as the inner solution 5 for the electrode contained in the indicating electrode body 1. The reference electrode 9 which is inserted into the reference electrode body 2 is the same as the inner electrode 6. The reference electrode body 2 is provided with a liquid junction 8 adapted to provide communication between the solution 7 for the reference electrode and the sample solution 3. When the potential difference between the inner electrode 6 and the reference electrode 9 is measured, the potential difference between the inner electrode 6 and the electrode inner solution 5 and the potential difference between the reference electrode 9 and the electrode inner solution 7 are equal to each other and are offset. The reference electrode solution 7 and the sample solution 3 possess substantially equal electric potentials because they communicate with each other through the liquid junction 8 (although there may be generated a very slight liquid junction potential, to be very strict). Consequently, the change in the potential difference thus measured is proportional to the logarithm of the change in the objective ion activity in the sample solution.

When the blood as a sample is measured for its $Cl^-$ ion activity, for example, in a test apparatus of the construction illustrated in FIG. 1, a 0.1 M/L aqueous solution of KCl is used as the electrode inner solutions 5, 7 and silver wires coated with a AgCl layer are inserted one each as the inner electrode 6 and the reference electrode 9. A monovalent anion-exchange membrane is used as the ion-exchange membrane.

The measurement of the blood for its $Na^+$ ion concentration can be effectively carried out by using the apparatus of the construction of FIG. 1, except that a cation-exchange membrane is used to cover the open bottom of the indicating electrode body 1 and an aqueous NaCl solution is used as the inner solution 5 for the electrode.

Figure 3:
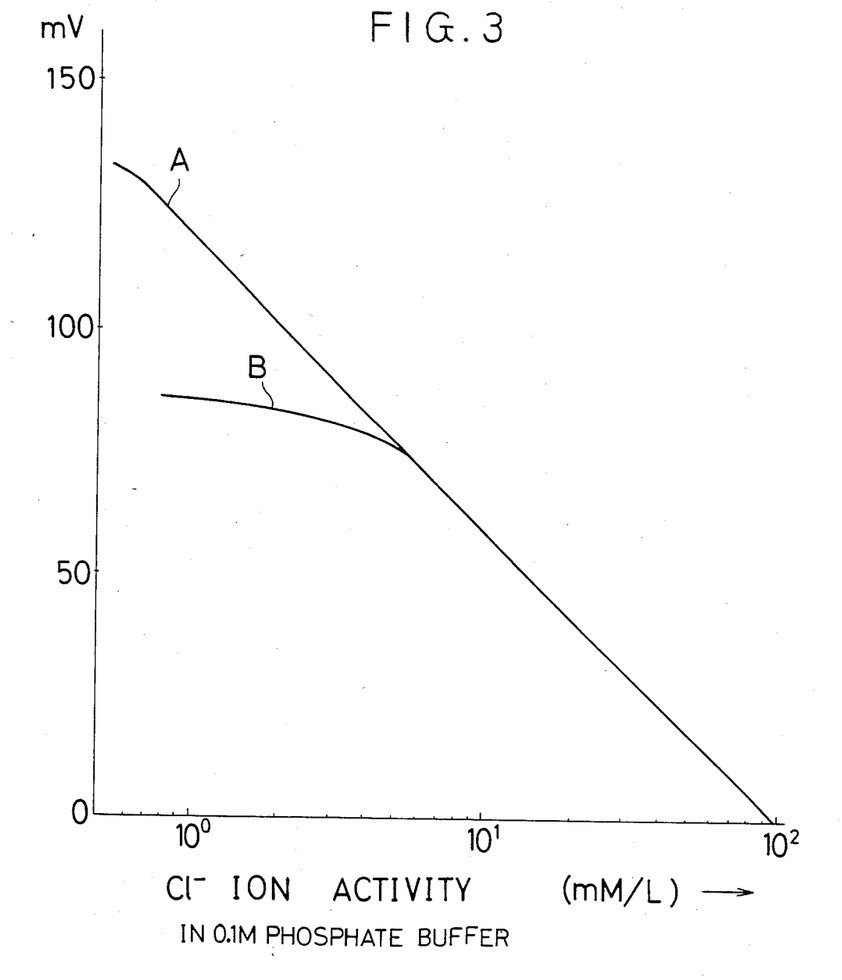
FIG. 3 is a graph showing the potential response for chloride ion activity of typical electrodes of this invention used for the measurement of an ion activity.

In the graph of FIG. 3, the curve A represents the potential difference, mV, between the electrodes 6, 9 as the function of the KCl concentration of the 0.1 M phosphate buffer solution used as the sample in a test apparatus using, as the electrode membrane 4 a commercially available anion-exchange membrane (a styrene copolymer membrane having a thickness of 0.1 mm, containing quaternary ammonium chloride and produced by Tokuyama Soda Co., Ltd., Tokyo, Japan) which has been immersed in a 30% aqueous solution of dodecylbenzene sulfonic acid at 60° to 70° C. for two to three hours. The potential difference shows a satisfactory linearity relative to the logarithm of the KCl activity within the KCl concentration range of from $10^0$ to $10^2$ (mM/L). The curve B represents the results obtained by repeating the procedure described above, except that the ion-exchange membrane is used in its untreated state as the electrode membrane 4. The sample is a phosphate buffer solution containing $PO_4^{3-}$ and $HPO_4^{2-}$. In the zone of low KCl concentration, the curve is bent down because the ions of such phosphates impede the measurement (namely, the membrane is sensitive to these ions), making it impossible to continue the measurement for the $Cl^-$ concentration. From these results, it is noted that the aforementioned pretreatment serves to deprive the membrane of its sensitivity to the multivalent anion.

Figure 4:
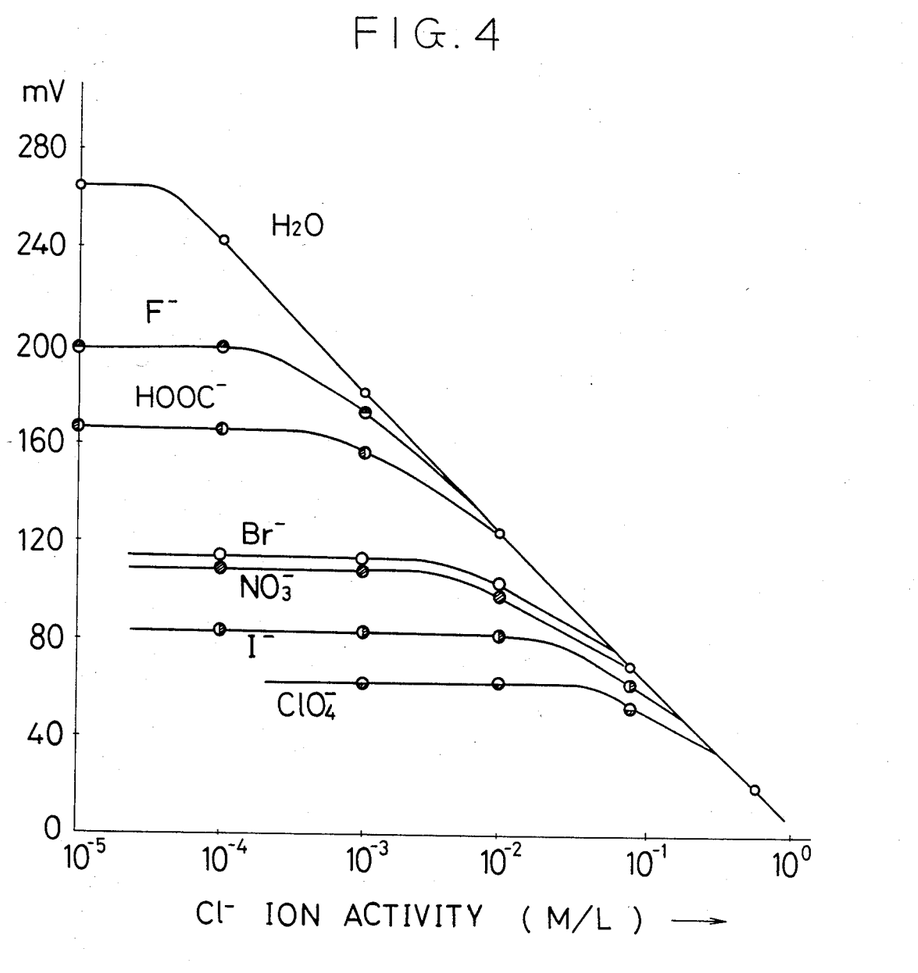
FIG. 4 is a graph showing the interfering effect of various anions against the potential response of chloride ion in the use of the electrode of this invention.

The curves in the graph of FIG. 4 represent the data obtained by using the same monovalent anion selective membrane as that used in the test giving the results of FIG. 3. They indicate that the ion selectivity of the electrode membrane is improved by the pretreatment of the anion exchange membrane with a sulfonic acid compound and that the membrane shows good selectivity to a specific group of all the monovalent anions tested. The horizontal axis of the graph is the scale for the $Cl^-$ ion activity (with an aqueous solution of KCl used as the sample) and the vertical axis is the scale for the potential difference between the electrodes 6, 9 in the construction of FIG. 1. The curve $H_2O$ represents the data obtained by using an aqueous solution of pure KCl as the sample. The curve $F^-$ represents the data obtained by using, as the sample, an aqueous solution of KCl incorporating additionally a fluoride ion $F^-$ in a concentration of 10 m M/L. From this curve, it is noted that the obstruction of $F^-$ appears in the zone of low $Cl^-$ ion concentration. By the same token, the curve $HCOO^-$ represents the data obtained of the aqueous KCl solution containing formic acid in a concentration of 10 m M/L, the curve $Br^-$ containing bromide ion, the curve $NO_3^-$ containing nitric acid ion, the curve $I^-$ containing iodide ion, and the curve $ClO_4^-$ containing perchloric acid ion respectively in a concentration of 10 mM/L.

The $Cl^-$ determination in the use of the present electrode of this invention is essentially based on the measurement of electrical potential appearing on the phase boundary layer between the outside of the membrane and the electrolytic solution, as explained above. As a rule, when an anion exchange membrane is immersed in solution, a diffuse electrical double layer is formed and the so-called "Donnan potential" appears on the phase boundary. One must consider an ion exchange membrane fixed only by anion exchange group, that is, the quaternary ammonium ion based membrane without the sulfonic acid group. In this system, the quaternary ammonium ion is a fixed ion group, $Cl^-$ and other interfering anions are counterions, and the cations (e.g., $H^+$, $K^+$, and $Na^+$) are the coions. In the development process of the Donnan equilibria, the rate-determining step will be controlled by the diffusions of movable counterions and coions across the boundary layer. As long as the ion exchange group fixed on the surface of the membrane is the anion exchange group having the positive charge, the cations (coions) are not naturally contributive. The counterions having a larger diffusion coefficient (e.g., $NO_3^-$ or $Cl^-$) diffuse more readily across a developing double layer and control the Donnan potential compared to the counterions having a smaller diffusion coefficient (e.g., $HCOO^-$ or $HPO_4^{2-}$). The Donnan potential developed by the diffusion of the former anions will bring a reverse effect to prevent the latter from normally diffusing across the boundary layer. It was experimentally confirmed that the potential responses plotted against the logarithms of the latter anion activities (log $a_i$) showed a closed Nernstian slope when the former anion activities were extremely diluted. Secondly, it must be considered that on the present quaternary ammonium based membrane a small amount of the fixed cation exchange group having the negative charge (e.g., sulfonic acid group) is partially distributed in addition to any sufficient amount of fixed anion exchange group (e.g., quaternary ammonium ion), and attention should be paid to the cation exchange reaction. The fixed cation exchange group's connection is that the counterions are cations (e.g., $H^+$, $K^+$, and $Na^+$) and coions are anions (e.g., $Cl^-$ and other interfering anions such as $HCOO^-$ and $HPO_4^{2-}$). As a rule, the fixed cation exchange group (sulfonic acid group) excludes the coions from the ion exchanger and the anions are prevented from diffusing across the boundary layer. This tendency will be strong in any smaller diffusion coefficient anions. Along with this tendency, the so-called Sieve action or a modification of the fixed charge density made by the distributed cation exchange groups on the surface of ion exchanger may also be effective to the movements of these anions. Smaller diffusion coefficient anions, after all, are considerably hampered in diffusing across the boundary layer and less contributive to the formation of the Donnan potential. Because the present membranes are essential anion exchange membranes including any sufficient amount of quaternary ammonium chloride, their Donnan potentials are controlled by $Cl^-$ activities, and then the $Cl^-$ selectivity for interfering anions (the smaller diffusion coefficient anions) will be improved according to the above-mentioned reasons. For the quaternary ammonium ion based membranes with and without the sulfonic acid group, the sequence of the $K_{Cl \cdot i}$ values for various interfering ions dissolved with $Cl^-$ in aqueous solution was $$ClO_4^- > SCN^- > I^- > Br^- > NO_3^- > ClO_3^- >$$
$$(Cl^-) > HCOO^- > HCO_3^- > F^- > H_2PO_4^- > CH_3COO^- >$$
$$S^{2-} > C_2O_4^{2-} > SO_4^{2-} > HPO_4^{2-} > B_4O_7^{2-}.$$

Figure 2:
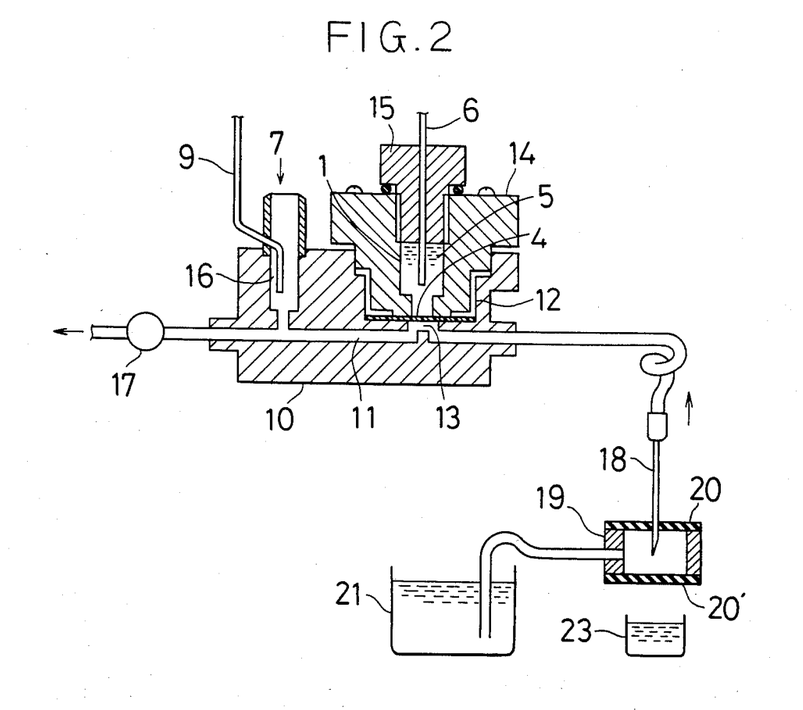
FIG. 2 is a longitudinal cross section showing in side elevation a typical apparatus using the electrode of this invention for the measurement of an ion activity.

It was also found that this sequence agreed well with the sequence of the diffusion coefficient, $D_{inf}$, for these anions, and the relation of the $D_{inf}$-log $K_{Cl \cdot i}$ plot was very close to a linear form. Furthermore, it was confirmed that the $D_{inf}$-log $K_{Cl \cdot i}$ plot for the membrane with sulfonic acid group showed a steeper line than that for the membrane without sulfonic acid group. The $D_{inf}$ means, here, the diffusion coefficient for infinitely diluted solution, but the linearity of the $D_{inf}$-log $K_{Cl \cdot i}$ plot will be more closely formed with the practical values of diffusion coefficients for these anions. On the other hand, the membranes in which the sulfonic acid group was overabundant, presented the characteristics of a cation exchange membrane, and then the interfering potential response caused by the codissolved cations increased gradually. FIG. 2 illustates one typical experimental apparatus using the electrode of the present invention for the measurement of an ion activity. In the diagram, 10 denotes a main block through which a path 11 for the flow of the solution subjected to the measurement pierces in a horizontal direction. In the upper surface of the main block 10, a recess 12 is formed. Part of the path 11 has its opening 13 in the bottom of the recess 12. On the bottom of the recess 12, an anion selective electrode membrane 4 pretreated as described above with the dodecylbenzene sulfonic acid is stretched to cover the opening 13. In the recess 12, a plug 14 is helically inserted. This plug 14 is provided with a vertical perforation 1 at the position opposite the opening 13 at the center. This perforation corresponds to the indicating electrode body 1 in FIG. 1. The lowermost surface of the plug 14 presses the anion selective electrode membrane 4 against the bottom of the recess 12. Consequently, the electrode membrane 4 concurrently serves as a packing for liquid-tightly partitioning the perforation 1 and the path 11 from each other. The perforation is filled with a 0.1 M/L aqueous solution of KCl as the electrode inner solution 5. In this solution is inserted the indicating electrode 6. This electrode is formed by coating a silver wire with a layer of AgCl. By 15 is denoted a stopper for the perforation 1 in the plug 14. To the left of the recess 12, a passage 16 is bored perpendicularly to the path 11. Through this passage 16, the same 0.1 M/L aqueous KCl solution 7 as the electrode solution 5 is passed into the path 11. The sample solution flows from the righthand side of the path and joins the KCl solution running in through the passage 16. The mixture flows out of the path 11 through the lefthand end. Into the passage 16, the reference electrode 9 is inserted laterally. Similarly to the indicating electrode 6, this reference electrode 9 is formed by coating a silver wire with a layer of AgCl. The solution running in through the passage 16 is the reference electrode solution. The reference electrode 9 is inserted into this electrode solution and is never allowed to come into contact with the sample solution. Denoted by 17 is a pump for delivering the sample solution. This pump is provided on the suction side thereof with a syringe 18. By 19 is denoted a container having the upper and lower sides thereof covered with rubber membranes 20, 20'. This container communicates with the standard solution reservoir 21. The rubber membranes 20, 20' each contain one straight cut. The cuts are tightly closed by the elasticity of the rubber and do not permit leakage of solution. Normally, the syringe 18 is passed through the cut in the rubber membrane 20 until the leading end thereof falls halfway in the distance between the rubber membranes 20, 20'. The pump 17 draws the standard solution for calibrating the electrode potential from the reservoir 21 and forwards it to the path 11. The standard solution is a 0.1 M/L aqueous KCl solution. While this solution is flowing through the path 11, the ion selective electrode membrane 4 and the reference electrode 9 both are exposed to contact with the 0.1 M/L aqueous KCl solution. Thus, the potential difference between the electrodes 6, 9 is zero and the concentration meter ought to indicate 0.1 (M/L). In this way, therefore, the meter is adjusted to eliminate possible instrumental error. A sample 23 held in a container is brought in and placed under the container 19. The sample may be the whole blood taken from a subject, the plasma obtained by removing corpuscular components from the whole blood, or the serum obtained by further removing fibrins from the plasma or the cerebrospinal fluid. When the syringe 18 is lowered until the leading end thereof passes through the cut in the rubber membrane 20' and enters the sample 23, the pump 17 draws the sample 23. After that, the syringe 18 is returned to its original position. Consequently, the sample 23 is forwarded to the path 11 for a short time. Subsequently, the standard solution begins to flow through the path 11. While the sample remains in contact with the membrane 4, the meter indicates the $Cl^-$ ion concentration of the sample. Each time a new sample is brought in, the procedure described above is repeated. While no sample is flowing through the path 11, the standard solution flows through the path 11 and washes the membrane 4 to remove from the membrane the residue of the previous sample adhering to the membrane. If the pump continued working while the syringe 18 is passed through the rubber membrane 20' and plunged into the sample and also while the syringe 18 is returned to its original position, it would draw in air and deliver it to the path 11. To avoid this trouble, therefore, the pump is kept at rest. If the pump is allowed to drawn in air for a very brief time after the syringe 18 has passed through the rubber membrane 20', then the bubbles will be passed through the path 11 and the standard solution will be enabled to give more effective washing to the membrane 4.

The structure and operation of the apparatus in accordance with the invention were explained as above. When the electrode of the invention is incorporated into a commercially available ion meter (e.g., CIM-101A, Shimadzu Corporation, Kyoto, Japan) which however is modified to some extent, it can provide advantages such as automatic cleaning, digital display and printout of measured results in m M/L, and correction of temperature in the Nernstian equation.

To demonstrate the effect of this invention, the method using the ion selective electrode of this invention was compared with the coulometric method. Since the coulometric analysis does not permit use of whole blood, the plasma isolated from the whole blood was subjected to the test. For the ion electrode method in accordance with this invention, both whole blood and the isolated plasma were used. The detail of the comparative experiment follows. An improved version of the aforementioned Shimadzu ion meter was used as the apparatus for the ion electrode method of this invention. The results were as follows.

Sample blood was collected from 38 hospital patients and the $Cl^-$ concentration was measured by the ion electrode method using about 250 μL of whole blood from each of the samples. Plasma was then extracted from the remainder (about 500 μL) of the sample blood by centrifugal methods. Attempts were made to measure the plasma by the present ion electrode method and also by argentometric coulometry. Thus, chloride ion was determined by three different methods for each blood sample. The values of $Cl^-$ in whole blood, X, and those in plasma, Y, determined by the present method, showed satisfactory agreements; the correlation coefficient was 0.997 and the regression line between them was $X = 0.968Y + 3.121$. In the measurement of plasma, the values obtained with the present ion electrode method, Y, and with argentometric coulometry, Z, also conformed satisfactorily, the correlation coefficient was 0.981 and the regression line was $Y = 1.031Z - 3.420$. Although it was impossible to compare the present method with any other method for whole blood measurement, the finding is that this method enables the prompt determination of $Cl^-$ concentration in blood using less than 250 μL sample without the necessity for complicated pretreatment such as separation of serum of plasma.

During the measurement of the $Cl^-$ activity in the blood sample by the method of this invention, effects of various organic compounds upon the measurement were also studied. The results were as follows.

TABLE 1

The Effect of Various Organic Interferents Contained in Blood samples on the Cl⁻ Determination with the CI-ISE*[a]

| Interferents | Normal concn. in blood*[b] | Tested concn. |
|---|---|---|
| *Enzymes* | | |
| catalase | 2.0–4.8 g/L | 25 g/L |
| lipase | 17–280 IU/L | 1400 IU/L |
| *Proteins* | | |
| albumin | 35–55 g/L | 50 g/L |
| fibrinogen | 2–6 g/L | 10 g/L |
| *Nitrogen Compounds* | | |
| creatinine | 6.4–11.2 mg/L | 50 mg/L |
| uric acid | 35–79 mg/L | 400 mg/L |
| alanine | 259–522 µM/L | 25 mM/L |
| arginine | 71–130 µM/L | 650 µM/L |
| glycine | 182–306 µM/L | 1.5 mM/L |
| glutamine | 500–830 µM/L | 4.2 µM/L |
| cystine | 50–82 µM/L | 410 µM/L |
| tyrosine | 52–114 µM/L | 570 µM/L |
| histidine | 58–111 µM/L | 500 µM/L |
| *Sugars* | | |
| glucose | 0.5–1 g/L | 5 g/L |
| glycogen | 12–162 mg/L | 360 mg/L |
| galactose | 0–200 mg/L | 1 g/L |
| lactose | 9–23 mg/L | 138 mg/L |
| *Lipid* | | |
| cholic acid | 0–3.4 mg/L | 34 mg/L |
| *Vitamins* | | |
| vitamin B$_6$ | 30–80 µg/L | 400 µg/L |
| L-ascorbic acid | 2–9 mg/L | 60 mg/L |
| β-carotene | 0.2–2 mg/L | 34 mg/L |
| nicotinic acid | 16–50 µg/L | 20 mg/L |
| *Hormone* | | |
| thyroxine | 45–115 µg/L | 5 mg/L |

*[a]In all cases, the effects of more than 0.5 mM Cl⁻ equivalent were not observed at the tested concentrations of the interferents.
*[b]See Handbook of Biochemistry by Yamakawa T. Ed., Tokyo Kagaku Dozin Co., Ltd. 1979, Vol I, p. 1541.

The electrode of this invention was also tested for its useful life. The results were as follows.

Figure 5:
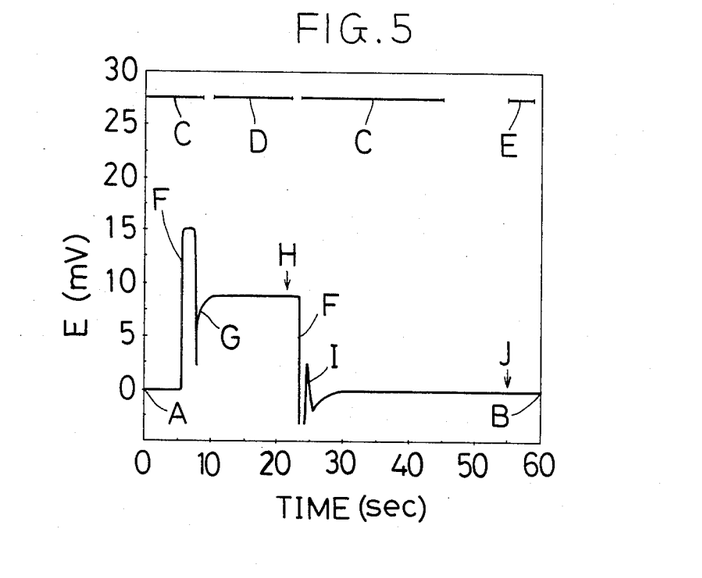
FIG. 5 is a graph recording result of potentials developed across the chloride ion selective electrode and reference electrode as a function of time during the measuring cycle: (A) start of cycle, (B) end of cycle, (C) cleaning period, (D) sample measuring period, (E) calculation, display and print, (F) air segments passing, (G) sample passing, (H) sample potential stored, (I) standard solution passing, (J) standard potential stored.
Figure 6:
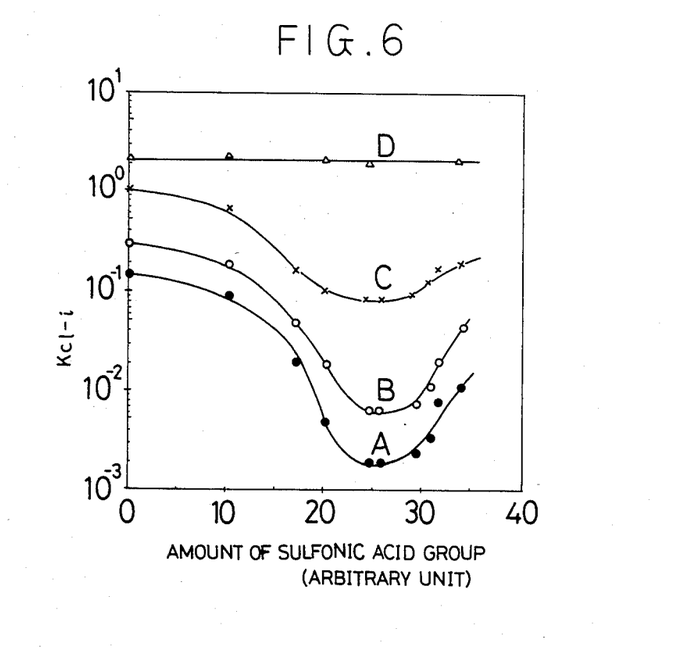
FIG. 6 is a graph showing the effects of a cation-exchange group upon the selective coefficients of typical interfering anions, (A) $HPO_4^{2-}$, (B) $SO_4^{2-}$, (C) $HCO_3^-$ and (D) $NO_3^-$.

If 1000 samples of blood were applied to the measurement with the modified Shimadzu analyzer for a month, this electrode will be expected to have at least a 15-month lifetime. This system has a mechanism whereby as the sample flow line is cleaned with aqueous solution and air for about 40 s (FIG. 5) after introducing 250 µL of a blood sample at a rate of about 1 mL/min (but before the start of the next measurement cycle). Such being the case, the life of the electrode may be expected to be considerably prolonged.

Now, the effect of this invention will be summarized below.

The electrode of this invention uses in its sensitive portion a solid membrane. Thus, it can be manufactured more easily and less expensively than the known electrodes using a liquid membrane (U.S. Pat. No. 3,429,785) and a heterogeneous membrane (U.S. Pat. No. 3,753,887). It further enjoys an advantage that it excels in chemical stability, toughness, ease of cleaning, and consistency of analytical accuracy. The electrode of this invention (particularly that which uses a solid membrane of amphoteric ion-exchange membrane) permits measurement of the activity of a specific ion which is present among a number of kinds of anions or cations. For example, it can directly measure the activity of the Cl⁻ ion alone in the blood in its original state as contained in the living body. Thus, the blood finds no use for centrifugation or incorporation of a chemical reagent. The analysis performed by the method of this invention enjoys high reproducibility and promptitude (less than 10 m sec).

What is claimed is:

1. A membrane electrode for insertion into an ion-containing liquid in a vessel for measuring the electromotive force generated across the interface of said electrode and said liquid for determining the ion activity of said liquid, said electrode comprising an electrode body for containing an inner electrolyte and an inner electrode and an amphoteric ion-exchange membrane forming at least part of the wall of the electrode body and separating the electrolyte and the ion-containing liquid for defining said interface, the membrane comprising a homogeneous mixture of ionic groups of opposite charges, one of the ionic groups being present in an amount significantly larger than the other.

2. An ion selective electrode for the potentiometric measurement of ion activity comprising an electrically conductive substrate coated with an amphoteric ion-exchange membrane, the membrane comprising a homogeneous mixture of ionic groups of opposite charges, one of the ionic groups being present in an amount significantly larger than the other.

3. An electrode of claim 1 or 2 in which the ratio of the exchange capacities of the ionic groups of opposite charges contained in the amphoteric ion-exchanger is in the range of from 40:60 to 0.5:95.5.

4. An electrode of claim 1 or 2 in which the ratio of the exchange capacities of the ionic groups of opposite charges is in the range of from 10:90 to 30:70.

5. An electrode of claim 1 or 2 in which a base polymer of the membrane is polystyrene, styrene-divinyl benzene copolymer or styrene-butadiene copolymer.

6. An electrode of claim 1 or 2 in which an anion-exchange group of the amphoteric ion-exchanger is trimethylammonium group, triethylammonium group or ammonium group and a cation-exchange group is sulfonic acid group, phosphonic acid group or carboxylic acid group.

7. An electrode of claim 6 in which the anion-exchange group is trimethylammonium group and the cation-exchange group is sulfonic acid group, the former being contained in a significantly larger amount than the latter.

8. An electrode of claim 1 or 2 adopted for the measurement of $HPO_4^{2-}$, $HCO_3^-$, $Cl^-$, $NO_3^-$, $SCN^-$ or $ClO_4^-$.

9. An electrode of claim 8 adopted for the measurement of $Cl^-$ or $NO_3^-$ in the living body.

10. An electrode of claim 8 adopted for the measurement of $Cl^-$ in whole blood of the living body.

11. An electrode of claim 1 or 2 adopted for the measurement of $Na^+$, $K^+$, or $NH_4^+$.

12. An apparatus for the selective determination of ion activity of an ion-containing liquid comprising a reference electrode; a membrane electrode comprising an electrode body containing an inner electrolyte and an inner electrode and an amphoteric ion-exchange membrane forming at least part of the wall of the electrode body and separating the electrolyte and the ion-containing liquid, the membrane comprising a homogeneous mixture of ionic groups of opposite charges, one of the ionic groups being present in an amount significantly larger than the other; circuit means for connecting the reference electrode with the membrane electrode and meter means for measuring the electromotive force generated across the interface of said membrane electrode and said liquid.

13. An apparatus for the selective determination of ion activity of an ion-containing liquid comprising a reference electrode; an ion selective electrode for the potentiometric measurement of ion activity comprising an electrically conductive substrate coated with an amphoteric ion-exchange membrane, the membrane comprising a homogeneous mixture of ionic groups of opposite charges, one of the ionic groups being present in an amount significantly larger than the other, circuit means for connecting the reference electrode with the ion selective electrode and meter means for measuring the electromotive force generated across the interface of said ion-selective electrode and said liquid.

14. An apparatus of claim 12 or 13 adopted for the measurement of $Cl^-$ in whole blood of the living body.

15. An apparatus for the selective determination of ion-activity in a sample solution comprising:

a vessel for receiving the sample solution;

a reference electrode comprising a first inner electrode and a reference electrode body for receiving a reference solution of desired ionic activity contacting both said inner electrode and the inside of said electrode body; said reference electrode body having an aperture for allowing communication between said reference solution and said sample solution;

an ion-selective electrode comprising a second inner electrode, an amphoteric ion-exchange membrane having inner surface and an outer surface and an electrode body for receiving a reference solution of desired ionic activity contacting both said second inner electrode and said inner surface of said membrane, said amphoteric ion-exchange membrane forming at least part of the wall of said electrode body for contacting the sample solution with said outer surface thereof; said amphoteric membrane comprising a homogeneous mixture of ionic groups of opposite charges, one of the ionic groups being present in an amount significantly larger than the other; means for electrically connecting said first inner electrode with said second inner electrode and meter means within said connection for monitoring the ion-activity of said sample solution.

* * * * *